United States Patent [19]

Narayanan et al.

[11] Patent Number: 5,231,070
[45] Date of Patent: Jul. 27, 1993

[54] LEACHING INHIBITION OF CROP TREATING CHEMICALS WITH LACTAM CONTAINING POLYMERS

[75] Inventors: Kolazi S. Narayanan, Palisades Park; Ratan K. Chaudhuri, Butler, both of N.J.

[73] Assignee: ISP Investments Inc., Wilmington, Del.

[21] Appl. No.: 843,325

[22] Filed: Feb. 28, 1992

[51] Int. Cl.$^5$ .................... A01N 25/10; A01N 25/22; A01N 25/24; A01N 43/70

[52] U.S. Cl. ................................. 504/113; 504/232; 504/324; 504/342; 71/DIG. 1

[58] Field of Search ............ 71/93, 115, 118, DIG. 1; 504/113

[56] References Cited

U.S. PATENT DOCUMENTS 3,886,125  5/1975  Chromecek ............... 71/DIG. 1
4,129,435 12/1978  Takematsu et al. ............ 71/93
5,022,917  6/1991  Allen ........................ 71/DIG. 1

*Primary Examiner*—Glennon H. Hollrah
*Assistant Examiner*—S. Marla Clardy
*Attorney, Agent, or Firm*—Marilyn J. Maue; Joshua J. Ward

[57] ABSTRACT

This invention relates to inhibiting leaching of crop treating chemicals into the ground water, aqua-system and surrounding soil of the treatment site by contacting the plant or plant site with an effective leach inhibiting, plant tolerating amount of a lactam containing polymer selected from the group of a crosslinked or non-crosslinked N-alkenyl lactam homopolymer or copolymer with a $C_2$ to $C_{30}$ comonomer selected from the group of an alkenoic acid; an alkenyl- anhydride, ester, ether, amino ester or amino amide and an alpha mono- or di-olefin, in which the lactam unit of the polymer is represented by the formula

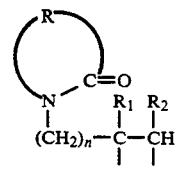

wherein R is $C_3$ to $C_6$ alkylene optionally substituted with $C_1$ to $C_{20}$ alkyl; $R_1$ and $R_2$ are each independently $C_2$ to $C_{20}$ alkyl or hydrogen and n has a value of from 0 or 2.

26 Claims, No Drawings

LEACHING INHIBITION OF CROP TREATING CHEMICALS WITH LACTAM CONTAINING POLYMERS

In one aspect, this invention relates to a polymeric material which is readily incorporated into an agrichemical formulation in order to inhibit leaching of the active agrichemical into the ground water and surrounding area of treatment In another aspect the invention relates to a composition for more effective use and reduced amounts of an active agrichemical.

BACKGROUND OF THE INVENTION

Agrichemical contamination is a growing concern since more than 12 different pesticides have been found in the ground water in at least 25 states in this country alone. Studies have shown that pesticide residues in ground water are increasing and are particularly severe where agronomic and horticultural crops are grown in permeable sandy soils or in locations which receive heavy rainfall. Among the chemicals which are particularly troublesome are herbicides such as bromacil, atrazine, metribuzin, dicamba and metolachlor, nematicides such as aldicarb, fungicides such as triforine, penconazole and insecticides such as bendiocarb, diazinone, chloropyrophos and ethion, which have been found in drinking water. Hence, there is an acute need to restrict the downward movement of pesticides, herbicides and other organic pollutants in the soil without reducing their agricultural efficacy.

Control of agrichemical leaching is a complex art which depends on many factors including rainfall, soil acidity and type, as well as plant tolerance. Various solutions to the problem have been proposed including controlled release formulations and encapsulated suspensions of the harmful active chemical. Surfactants have been employed for restricting the downward movement of urea herbicides such as diuron, linuron and monuron (see Weeds, by D. E. Bayer, Vol. 15, pages 249-252, 1967). The mobility of metribuzin in the soil has been reduced by the use of polyvinyl alcohol polymers, as discussed by C. L. McCormick and M. M. Fooladi, (1980) (Controlled Activity Polymers with Labile Bonds to Pendent Metribuzin in Controlled Release of Bioactive Materials, R. Baker, Academic Press, New York, pages 317-330). However, it was found that metribuzin formed covalent linkages with the polyvinyl alcohols which resulted in hindering its release from the alcoholic polymer for plant uptake. Certain pine craft lignins have shown some decrease in the leaching losses of atrazine and 2,4-D (see Weed Science, E. P. Dunigan and T. Macintosh, 1971, Volume 29 pages 279-282 and Controlled Release Technologies: Methods, Theory and Application by H. T. Dellicolli, 1980, Volume II, C. R. C. Press, Boca Raton, Fla., pages 225-234). Several other leaching inhibitors have been proposed; however, the chemicals currently used to inhibit downward movement have been found to be highly specific to certain chemical types and do not extend generally to plant treating agrichemicals of different chemical classes.

Accordingly, it is an object of this invention to provide a leach inhibiting chemical which is more broadly effective in preventing or inhibiting downward movement of various plant treating materials.

Another object of this invention is to provide an economically produced chemical which prevents or minimizes the movement of toxic chemicals in the soil and retains the plant treating agent in the root or immediate surrounding area of the soil where it is applied and where it is most effective.

Another object of this invention is to provide a leach inhibiting chemical composition which permits more efficient use of a crop treating agent in reduced amounts and which prevents or minimizes contamination of the aquasystem.

These and other objects of the invention will become apparent to one skilled in the art from the following description and disclosure.

THE INVENTION

For effective leaching control, a balance between hydrophilic and hydrophobic moieties in the control agent is required. This balance depends upon the structure and properties of the active component, i.e. the agrichemical and the components in its formulation with additives such as surfactants, certain carriers, emulsifiers, etc. This balance is achieved by means of the present leach controlling agent which is incorporated into the agrichemical formulation by blending, by complexing or by coprecipitating with the active agrichemical. Thus, in accordance with this invention, there is provided a leach inhibiting, lactam-containing polymer which is readily formulated with or incorporated into a plant treating agent which polymer is selected from the group of a crosslinked or non-crosslinked N-alkenyl lactam homopolymer or copolymer with a $C_2$ to $C_{30}$ comonomer selected from the group of an alkenoic acid; an alkenyl- anhydride, ester, ether, amino ester, amino amide; and an alpha mono- or diolefin and terpolymeric mixtures of the above monomers.

The lactam moiety of the polymer is represented by the formula

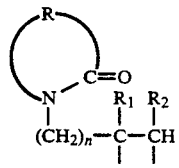

wherein R is $C_3$ to $C_6$ alkylene optionally substituted with $C_1$ to $C_{20}$ alkyl; $R_1$ and $R_2$ are each independently $C_2$ to $C_{20}$ alkyl or hydrogen and n has a value of from 0 or 2.

Examples of suitable lactam units include monocyclic lactams such as N-vinyl- and N-ethenyl- pyrrolidones, caprolactam; azacyclooctanones, as well as mono-, di- or tri- methyl, ethyl, octyl, hexadecyl, eicosyl, etc. ring substituted derivatives thereof. The N-alkenyl lactam polymers of this invention are those having a number average molecular weight of between about 5,000 and about 500,000, preferably between about 6,000 and about 150,000. The polymers also having a polydispersity* of from about 1 to about 8, most desirably about 2-6, are considered the best for providing uniform formulations of high efficiency. * Wt. Av. Molecular weight (Mw)/No. Av. Molecular Weight (Mn)

The above polymer/agrichemical composition is applied to the plant or surrounding soil area in a pre-emergent or post-emergent application and in an effective leach inhibiting, plant tolerating amount. In formulation with the active agrichemical, as little as 0.001 weight % of instant polymers, based on the total composition, is effective to inhibit leaching of various agrichemicals. However, a weight ratio of agrichemical to polymer of between about 0.1:1 and about 10:1 is recommended and between about 0.3:1 and about 2:1 is preferred The resulting agrichemical/leach inhibitor composition is formulated to provide a liquid, preferable of a sprayable consistency, and in some cases may require the addition of an inert diluent.

Of the present leach inhibitors, those containing between about 0 and about 90 weight % of the non-lactam comonomer are useful; however, those containing not more than 85 weight % of a comonomer are recommended for most plant species. Of the lactam species, substituted or unsubstituted N-vinyl pyrrolidonyl-containing polymers are preferred. Examples of the present leach controlling agents include $C_{20}$ alkylated N-vinyl pyrrolidone polymers (e.g. Ganex® V-220*); crosslinked N-vinyl pyrrolidone homopolymers, N-alkenyl pyrrolidone polymers with an alpha-olefin, such as propene or 1-butene (e.g. Ganex® P-904*); polyvinylpyrrolidinone/acrylic or methacrylic acid copolymer (e.g. ACP-1004*);

N-alkenyl pyrrolidone/propenoic acid copolymer;
N-alkenyl pyrrolidone/vinyl acetate copolymer;
N-alkenyl pyrrolidone/acrylic or methacrylic acid copolymer;
N-alkenyl pyrrolidone/methyl vinyl ether copolymer;
N-alkenyl pyrrolidone/butadiene copolymer;
N-alkenyl pyrrolidone/vinyl butyrate copolymer;
N-alkenyl pyrrolidone/maleic acid or anhydride copolymer;
N-alkenyl pyrrolidone/dimethylaminoethyl acrylamide copolymer; * supplied by ISP Technologies Inc., in Wayne, N.J., (a subsidiary of International Specialty Products Inc. quaternized N-alkenyl pyrrolidone/-dimethylaminoethyl acrylamide copolymer;
N-alkenyl pyrrolidone/dimethylaminoethyl methacrylate copolymer (copolymer 845);
quaternized N-alkenyl pyrrolidone/dimethylaminoethyl methacrylate copolymer;
N-vinyl pyrrolidone/N-vinyl caprolactam/dimethylaminoethyl methacrylate terpolymer (GAFFIC VC-713);
N-alkenyl caprolactam/dimethylaminoethyl methacrylate copolymer;
quaternized N-alkenyl caprolactam/dimethylaminoethyl acrylate copolymer;
N-vinyl pyrrolidone/eicosene copolymer;
1-ethenyl-2-pyrrolidinone/acetic acid ethenyl ester copolymer (e.g. P(VP/VA)S-630*);
N-alkenyl pyrrolidone/acrylic acid copolymer;
water-insoluble crosslinked polyvinylpyrrolidone or polyethenylpyrrolidone copolymers, and the like. * supplied by ISP Technologies Inc., in Wayne, N.J., (a subsidiary of International Specialty Products Inc.)

Particularly preferred are the vinyl pyrrolidone polymers shown in following Table A.

TABLE A

|  | Mn | Mw |
| --- | --- | --- |
| Linear poly(eicosenyl) N-vinyl eicosyl-pyrrolidone graft polymer (GANEX® V220) | 7,000–10,000 | 40,000–60,000 |
| N-vinylpyrrolidone/vinyl acetate copolymer (60/40) | 8,000–12,000 | 40,000–60,000 |
| Polyvinylpyrrolidone/ acrylic acid copolymer | 30,000–60,000 | 100,000–300,000 |

TABLE A-continued

|  | Mn | Mw |
| --- | --- | --- |
| (50/50) | | |
| Crosslinked polyvinylpyrrolidone (AGRIMER® XL) | 80,000–120,000 | 800,000–1,200,000 |
| N-vinylpyrrolidone/1-butene graft polymer (GANEX® P940) | 15,000–17,000 | 40,000–60,000 |
| Linear quaternized or non-quaternized N-vinylpyrrolidone/N-vinyl caprolactam/dimethylaminoethyl methacrylate terpolymer | >1,000,000* | |
| Linear quaternized or non-quaternized N-vinylpyrrolidone/dimethylaminoethyl methacrylate copolymer | >1,000,000* | |

*Mn/Mw

Representative crop treating agents which are commonly employed and which are controlled by the present leach inhibition agents include a wide range of herbicides, nematocides, insecticides, fungicides, plant growth promoting or regulating chemicals and other crop treating products. These include herbicides such as Dicamba, Alachlor, Aldicarb, Amiben, Arsenal, Assert, Atrazine, Bentazon, Bromacil, Bialaphos, Butylate, Carbofuran, Chloramben, Chlortoluron, Cyanazine, Banval, Cotoran, Dalapon, 2,4-D, Dicamba, Dinoseb, Diquat, Diuron, EDB, EPTC, Glyphosate, Glean, Hyvar, Linuron, Lexone, Lontrel, Monuron, Metribuzin, Mecoprop, Nortron, Norflurazon, Pramitol, Prometryn, Pyramin, Rhizobitoxin, Reflex, Scepter, Simazine, Sinbar, Tordon, Tentoxin, Terbacl, Trifluralin, urea, Velpar, etc.; growth regulants such as chloroethyl phosphonic acid; insecticides such as Azodrin, Diazinon, Dylox, Furadan, Metasystox, Mocap, Phosphamidon, Temik, Trigard, Vydate; nematodes such as Aldicarb; fungicides such as Triforine, Penconazole, Bendiocarb and others cited in the Agriculture Handbook, 2nd Ed., Royal Society of Chemistry, 1987. The agrichemicals which are particularly compatible and efficacious with the present leach inhibiting agents include atrazine, dicamba, bromacil, diuron, assert bisulfate, simazine, diazinone, perconazide, triforine and metolachlor.

All of the above agrichemicals are known and appropriate plant dosages and tolerances have been described for each product. Also their agrichemical formulations are well known and such are compatable with the present leach inhibiting agents in the aforementioned concentrations. The formulated active agents can be sprayed or misted to contact treating sites according to known procedures. Since the present lactam containing polymers are non-toxic, their incorporation into the formulation does not alter, and in some cases may reduce, the required effective dosage of agrichemical.

The inhibiting effect of the present polymers is achieved by their complexing, encapsulation, or blending with the agrichemical and applying to a plant site. In the leach inhibiting copolymers of the present invention, the lactam ring provides the hydrophilic moiety and the alkyl chain of the copolymer provides the hydrophobic portion. Correct balance between the hydrophilic and hydrophobic portions enable bonding of the agrichemical to the polymer and also cause a portion of the polymer to bind to the soil surface by either hydrophobic or hydrophilic interaction with organic matter in the soil. Thus, the polymer, together with the agrichemical, is more securely bound to the soil site where it is applied and leaching by rain water or irrigation is significantly reduced. In all instances, using the above active chemicals, a marked reduction, and in some cases, almost complete elimination of downward transmigration of the agrichemical from the immediate application area through the soil stratum is achieved.

The agrichemical formulations containing the present lactams can be directly prepared by simply mixing the lactam polymer into the standard agrichemical formulation or a preformed agrichemical concentrate thereof followed by recommended dilutions under ambient conditions. With certain agrichemicals, complexing with the polymer provides the highest leaching inhibition, with others, blending with the polymer achieves best results. The soil also has an important role in leaching such that the greatest leachability is found in highly porous, low organic Florida soils; whereas the loamy or clay soils of the midwest or northeast suffer least.

An advantage of the present leach inhibiting compounds is that they are non-specialized with respect to a certain group of agrichemical treating agents since the molecule contains both lipophilic and hydrophilic moieties. Also, the use of the present compounds affords more efficient use of the agrichemical since the later is retained in the immediate surrounding soil area or in the vicinity of the plant root system. Thus, somewhat smaller amounts of the agrichemical are often efficacious. Additionally the present lactams provide control of agrichemical leaching over a prolonged period of time so that less agrichemical need be applied in the next crop application. Another advantage is that the present compounds of lower molecular weight do not alter the dispersion properties of the agrichemical formulation and in some cases may enhance sprayability. In those cases where incorporation of the lactam polymer results in raising the viscosity to an undesirable level, an inert diluent such as a petroleum distillate, mineral oil, water, ethylene glycol, etc. can be added to the formulation. Various surfactants can also be included in the agrichemical formulation These include anionic sulfonates, e.g. lignin sulfonate, naphthalene/-formaldehyde condensate sulfonate, etc. and non-ionic alkoxylated phenols, e.g. ethoxylated or propoxylated nonyl or octyl phenols which can be present in an amount up to about 25 wt. % of the total composition.

Another advantage of the present invention is that the leach inhibiting formulation can also be applied as a powder for crop dusting; in which case the formulation is dried to a particulate solid before use. A further advantage of the present polymers is that they are non-toxic and environmentally safe; thus, they do not add to soil contamination. Additionally, the presence of lactam containing polymers adds to the organic content of the soil, thus benefiting future crops. These and many other advantages will be realized by the use of the present polymeric compounds.

Having thus generally described the invention, reference is now had to the accompanying examples which illustrate specific and preferred embodiments, but which are not to be construed as limiting to the scope of the invention as more broadly described above and in the appended claims.

EXAMPLES I–XVII

The following polymers 1–6 were mixed with agrichemicals A–C.

POLYMERS

1. Polyvinylpyrrolidone homopolymer (PVP K30).
2. $C_{20}$ alpha olefin alkylted polyvinylpyrrolidone containing 20 weight % PVP and 80 weight % $C_{20}$ alpha olefin.
3. 60 mole % vinylpyrrolidone/40 mole % vinyl acetate (PVP-VA 630) copolymer.
4. 50 weight % vinylpyrrolidone/50 weight % acrylic acid copolymer.
5. Crosslinked polyvinylpyrrolidone homopolymer.
6. $C_4$ alpha olefin alkylated polyvinylpyrrolidone containing 90 weight % PVP and 10 weight % $C_4$ alpha olefin.

AGRICHEMICALS

A. Dicamba
B. Atrazine
C. Metolachlor

The above agrichemicals possess widely disparate chemical properties as shown in Table B.

TABLE B

| Herbicide | CHEMICAL PROPERTIES OF HERBICIDES | | | |
|---|---|---|---|---|
| | Chemical Nature | Solubility (mg/L) | Half Life (d) | $K_{oc}$ | Leaching Potential+ |
| Atrazine | Basic | 33 | 60 | 100 | 17 |
| Dicamba | Acidic | 400,000* | 14 | 2 | 1.4 |
| Metolachlor | Nonionic | 530 | 90 | 200 | 22 |

+Leaching Potential is $K_{oc}$/half life × 10. The leaching potential varies inversely with the number value
*as dimethyl ammonium salt form The following mixing procedures X–Z were employed to prepare the polymer/agrichemical compositions.

X. The agrichemical (15 g.) and the polymer (15 g.) were dissolved in a common solvent and mixed at 55° C. for 4 hours; after which the solvent used for solubilizing was stripped off under reduced pressure and the solid polymer/agrichemical product (20–30 g.) was dried and recovered.

Y. The same as procedure X, except that, where the product is an amorphous gel, it was dissolved in a solvent and the final product is a liquid.

Z. The polymer was dispersed in a 10–15% solution of the agrichemical in ethanol (ETOH), tetrahydrofuran (THF) or a mixture thereof and the resulting dispersion or gel was heated to 45±5° C. for 4 hours with agitation. The solvent mixture was then stripped off under vacuum and the product recovered.

The coprecipitated or complexed products of the above experiments are reported in following Table I.

TABLE I

| Example No. | Agrichemical | Polymer | Initial Agrichemical wt. ratio | Prep. Method | Solubilizing Agent | State of Final Product/Solvent | Assay* |
|---|---|---|---|---|---|---|---|
| I | A | 1 | 1:1 | X | MeOH | solid/none | 56.4 |
| II | A | 2 | 1:1 | Y | THF | liquid/THF | 10.1 |
| III | A | 3 | 1:1 | X | MeOH | solid/none | 54.4 |

TABLE I-continued

| Example No. | Agrichemical | Polymer | Initial Agrichemical wt. ratio | Prep. Method | Solubilizing Agent | State of Final Product/Solvent | Assay* |
| --- | --- | --- | --- | --- | --- | --- | --- |
| IV | A | 4 | 1:1 | Z | EtOH | solid/none | 51.5 |
| V | A | 5 | 1:1 | Z | EtOH | solid/none | 49.4 |
| VI | B | 1 | 1:1 | X | EtOH/THF (1:1) | solid/none | 46.4 |
| VII | B | 2 | 1:1 | X | THF | solid/none | 50 |
| VIII | B | 3 | 1:1 | X | THF | solid/none | 47.3 |
| IX | B | 4 | 1:1 | Z | THF/EtOH (72:28) | solid/none | 49.6 |
| X | B | 5 | 1:1 | Z | THF/EtOH (1:1) | solid/none | 50.6 |
| XI | C | 1 | 1:1 | Y | ETOH | liquid/ETOH | 10.2 |
| XII | C | 2 | 1:1 | Y | THF | liquid/THF | 10.6 |
| XIII | C | 3 | 1:1 | Y | ETOH | liquid/ETOH | 9.8 |
| XIV | C | 4 | 1:1 | Z | ETOH/H2O 1:1 | solid/none | 54.2 |
| XV | A | 6 | 1:1 | X | EtOH | solid/none | 57.0 |
| XVI | B | 6 | 1:1 | Y | EtOH | liquid/EtOH | 10.3 |
| XVII | C | 6 | 1:1 | Z | EtOH/THF (1:1) | solid/none | 52.3 |

*by UV analysis, % Agrichemical

EXAMPLES XVIII-XXXI

The above polymer/agrichemicals were each targeted with 8,500 cpm* of the corresponding radioactive $^{14}C$ doctored agrichemical and then introduced at a rate of 5 lbs/acre into the top of an open bottom plexiglass 7 cm diameter, 8 cm long column containing 450 g of Polk County Florida surface soil. Then, water at room temperature was added in 4 increments of 125 ml. each to simulate 4 pore volumes i.e. normal rain conditions. The $^{14}C$ activity in each of the effluent solutions was assayed and the relative % of agrichemical recovered compared to 100% recovery in the absence of the present polymer is reported in the following Table II. * curie/million

TABLE II

| | | % Agrichem in Effluent | | | | |
| --- | --- | --- | --- | --- | --- | --- |
| Example | Sample of Ex. | First Pore V. | Second Pore V. | Third Pore V. | Fourth Pore V. | Total |
| XVIII | 2 | 15.0 | 21.3 | 12.6 | 10.1 | 45.5 |
| XIX | 4 | | | | | |
| XX | 5 | | | | | |
| XXI | 1 | | | | | |
| XXII | 7 | 3.9 | 30.4 | 22.7 | 15.2 | 74.4 |
| XXIII | 8 | 3.8 | 32.6 | 24.4 | 17.4 | 76.0 |
| XXIV | 9 | | | | | |
| XXV | 10 | | | | | |
| XXVI | 11 | 11.7 | 43.5 | 21.32 | 8.49 | 85.0 |
| XXVII | 13 | 7.02 | 17.5 | 20.10 | 13.52 | 58.2 |
| XXVIII | 14 | | | | | |
| XXIX | 15 | 5.2 | 31.4 | 24.8 | 5.70 | 67.1 |
| XXX | 16 | 5.8 | 36.8 | 23.7 | 13.5 | 79.74 |
| XXXI | 17 | 13.2 | 42.8 | 17.16 | 8.06 | 81.2 |

The above data shows that by the fourth wash only a minimal amount of the agrichemical was leached out of the immediate vicinity (to a 8 cm depth) of the soil application site.

EXAMPLES XXXII-XLVIII

Blends of the above polymer/agrichemicals in commercial formulations containing surfactant, emulsifier and diluent were prepared as follows.

The polymer (5.0 g on 100 wt. % basis) was added to each of the following commercial agrichemical liquid formulations D-F to provide a weight ratio of 1:1 polymer to agrichemical and diluted with water to form a solution containing 10 wt. % polymer and 10 wt. % agrichemical.

D. Banvel herbicide containing 40% Dicamba in 4 lbs/gal of water
E. Aatrex 4L containing 40.8% Atrazine
F. Dual containing 86.4% Metolachlor The resulting solutions were then targeted with 8,500 cpm of radioactive $^{14}C$ agrichemical of the same species. The resulting mixtures were individually added to the top of a separate column similar to that above at a rate of 5 lbs. agrichemical/acre and the leachates from each of the 4 water washings were collected and analyzed.

The column employed in this study was used at bulk density of soil at packing. Each pore volume of water applied on the top of the soil column was equivalent to 3.2 cm (1.28 inch) of rainfall. The amount of herbicide leached was calculated on the basis of $^{14}C$-herbicide applied and recovered from the leachate. The difference between these two values represented that which was adsorbed by the soil.

Controls were run under exactly the same conditions with the same agrichemicals, except that the inhibiting polymer of this invention was omitted. In each control 100% leaching of agrichemical occurred. The analysis of the leachate from each of the 4 pore volumes is reported in following Table III.

TABLE III

| | | Relative % of Agrichemical Recovered Compared To 100% Leaching with Control* | | | | | |
|---|---|---|---|---|---|---|---|
| Example | Polymer | Agrichemical | 1st Pore | 2nd Pore | 3rd Pore | 4th Pore | Total |
| XXXII | 1 | D | 9.2 | 46.4 | 4.0 | 0.75 | 60.4 |
| XXXIII | 2 | D | 15.9 | 42.5 | 19.3 | 7.70 | 85.4 |
| XXXIV | 3 | D | 15.7 | 51.6 | 6.9 | 1.4 | 75.6 |
| XXXV | 4 | D | 9.1 | 42.6 | 14.9 | 3.2 | 69.8 |
| XXXVI | 5 | D | 1.5 | 36.3 | 13.9 | 8.3 | 60.0 |
| XXXVII | 1 | E | 1.72 | 36.97 | 25.66 | 19.39 | 83.74 |
| XXXVIII | 2 | E | 6.06 | 23.33 | 23.03 | 21.92 | 74.34 |
| XXXIX | 3 | E | 1.52 | 29.6 | 23.84 | 15.15 | 70.11 |
| XL | 5 | E | 4.14 | 22.12 | 28.38 | 23.43 | 78.07 |
| XLI | 1 | F | 15.24 | 19.85 | 23.24 | 14.02 | 72.35 |
| XLII | 2 | F | 33.8 | 21.96 | 9.28 | 11.33 | 76.35 |
| XLIII | 3 | F | 22.02 | 25.75 | 18.44 | 8.13 | 74.34 |
| XLIV | 4 | F | 16.07 | 36.49 | 15.88 | 7.17 | 75.61 |
| XLV | 5 | F | 11.97 | 30.92 | 15.11 | 9.03 | 67.03 |
| XLVI | 6 | D | 49.9 | 30.3 | 3.0 | 0.47 | 83.7 |
| XLVII | 6 | E | 3.54 | 31.72 | 25.76 | 12.53 | 73.55 |
| XLVIII | 6 | F | 27.14 | 21.0 | 10.12 | 17.03 | 75.29 |

*By $^{14}$C activity assay using Scintillation counter, % Agrichemical

EXAMPLES XLIX-LXV

Bioassays of selected samples (i.e. products of Examples XXXII, XXXIII, XXXV-XXXIX, XLI-XLVI and XLVIII) were made and results reported in Table IV. The procedure for these examples is as follows.

The indicated polymer/agrichemical formulation was introduced into a 130 cm×10 cm soil packed column. In these experiments, 2.5 cm simulated rainfall was used for Dicamba 7.5 cm simulated rainfall for Atrazine and Metolachlor was employed by adding water at the rate of 1.5 cm/hr. After leaching, the columns were allowed to drain overnight and split longitudinally into two halves. Each half was planted with alfalfa or rye grass (as indicated) in 5 cm spaced rows. The % injury as a function of herbicide movement at different heights are shown in Table IV.

At every 15 cm from bottom of the column, a ridge of silicone was applied on the inside wall of each half of the column to prevent "edge flow" of water along the soil-wall interface. A PVC end-cap with a small drain hole was fitted to the bottom of the column and the columns were packed with Florida soil from respective depths to provide a Florida soil profile. Soil-packed columns were kept in upright position and the soil was saturated with water and allowed to drain overnight; after which the commercial formulation of herbicide (5 kg ai/ha) with or without polymers (5 kg/ha) was introduced to the top of the column. A 2 ml solution of each treatment was applied uniformly on the soil surface as several drops using pasteur pipet. Columns were leached by pouring distilled water over filter paper placed on the soil surface to ensure uniform distribution of water and leaching was measured at 15, 30, 45, 60 and 60+ cm depths.

TABLE IV

| | % Alfalfa Injury (Application rate 5 kg/ha or 4.5 lbs/acre) | | | | | | |
|---|---|---|---|---|---|---|---|
| | Sample % | Column Depth (cm) | | | | | Total % |
| Example | of Ex. | 0-15 | 15-30 | 30-45 | 45-60 | 60-120 | Decrease |
| XLIX | 32 | 100 | 100 | 100 | 83 | 0 | 4 |
| L | 33 | 100 | 100 | 100 | 83, 67 | 0 | 4 and 8 |
| LI | 35 | 100 | 100 | 100 | 67 | 0 | 8 |
| LII | 36 | 100 | 100 | 100 | 75 | 0 | 6 |
| LIII | 46 | 100 | 100 | 100 | 83 | 0 | 4 |
| LIV | Controls with no polymer | 100 | 100 | 100 | 100 | — | 0 |

| | % Rye Grass Injury (Application rate 10 kg/ha or 8.9 lbs/acre) | | | | |
|---|---|---|---|---|---|
| | Sample % | Column Depth (cm) | | | Total % |
| Example | of Ex. | 0-15 | 15-30 | 30-120 | Decrease |
| LV | 41 | 100 | 75 | 0 | 12.5 |
| LVI | 42 | 100 | 67 | 0 | 25 |
| LVII | 43 | 100 | 83 | 0 | 8.5 |
| LVIII | 44 | 100 | 83 | 0 | 8.5 |
| LVIX | 45 | 100 | 58 | 0 | 21 |
| LX | 48 | 100 | 50 | 0 | 25 |
| LXI | Controls with no polymer | 100 | 100 | 0 | 0 |

| | % Alfalfa Injury (Application rate 5 kg/ha or 4.5 lbs/acre) | | | | |
|---|---|---|---|---|---|
| | Sample % | Column Depth (cm) | | | Total % |
| Example | of Ex. | 0-15 | 15-30 | 30-120 | Decrease |
| LXII | 37 | 100 | 92 | 0 | 4 |
| LXIII | 38 | 100 | 92 | 0 | 4 |
| LXIV | 39 | 100 | 75 | 0 | 12.5 |
| LXV | Controls | 100 | 100 | 0 | 0 |

TABLE IV-continued with no polymer

EXAMPLES LXVI-LXXXVIX

The following polymers 7-8 were mixed with agrichemicals A-C using procedure X or Y.

Polymers

7. Quaternized Copolymer 845 (97% N-vinyl pyrrolidone/3% dimethylaminoethyl methacrylate quaternized with citric acid) as a 20% aqueous solution.
8. GAFFIX ® VC-713 (terpolymer of N-vinyl pyrrolidone/N-vinyl caprolactam/dimethylaminoethyl methacrylate) as a 37% ethanol solution.

TABLE V

| Example No. | Agrichemical | Polymer | Initial Agrichem Wt. Ratio | Prep Method | Solubilizing Agent | State of Final Product | Solvent | Assay* by UV Analysis % Agrichem |
| --- | --- | --- | --- | --- | --- | --- | --- | --- |
| LXVI | A | 7 | 1:1 | X | EtOH | solid | — | 51.8 |
| LXVII | A | 7 | 0.6:0.4 | X | EtOH | solid | — | 55.6 |
| LXVIII | A | 7 | 0.7:0.3 | X | EtOH | solid | — | 78.9 |
| LXIX | A | 7 | 0.4:0.6 | X | EtOH | solid | — | 38.9 |
| LXX | A | 8 | 1:1 | X | EtOH | solid | — | 51.6 |
| LXXI | A | 8 | 0.6:0.4 | X | EtOH | solid | — | 58.6 |
| LXXII | A | 8 | 0.7:0.3 | X | EtOH | solid | — | 76.1 |
| LXXIII | A | 8 | 0.8:0.2 | Y | EtOH | liquid | EtOH | 16.3 |
| LXXIV | B | 7 | 1:1 | X | THF/EtOH | solid | — | 47.53 |
| LXXV | B | 7 | 0.6:0.4 | X | THF/EtOH | solid | — | 55.3 |
| LXXVI | B | 7 | 0.7:0.3 | X | THF/EtOH | solid | — | 59.2 |
| LXXVII | B | 7 | 0.4:0.6 | Y | THF/EtOH | liquid | THF | 57 |
| LXXVIII | B | 8 | 1:1 | X | THF | solid | — | 48.4 |
| LXXIX | B | 8 | 0.6:0.4 | X | THF | solid | — | 49.3 |
| LXXX | B | 8 | 0.7:0.3 | X | THF | solid | — | 59.3 |
| LXXXI | B | 8 | 0.4:0.6 | X | THF | solid | — | 32.4 |
| LXXXII | C | 7 | 1:1 | Y | EtOH | liquid | EtOH | 10.2 |
| LXXXIII | C | 7 | 0.6:0.4 | Y | EtOH | liquid | EtOH | 10.8 |
| LXXXIV | C | 7 | 0.7:0.3 | Y | EtOH | liquid | EtOH | 11.9 |
| LXXXV | C | 7 | 0.4:0.6 | Y | EtOH | liquid | EtOH | 7.3 |
| LXXXVI | C | 8 | 1:1 | Y | EtOH | liquid | EtOH | 10.3 |
| LXXXVII | C | 8 | 0.6:0.4 | Y | EtOH | liquid | EtOH | 12.1 |
| LXXXVIII | C | 8 | 0.7:0.3 | Y | EtOH | liquid | EtOH | 13.9 |
| LXXXIX | C | 8 | 0.4:0.6 | X | EtOH | solid | — | 37.1 |

UV analysis % Agrichemical
*The ratio is by weight of solid polymer and 0.1.

EXAMPLES XC-XCIII

The above polymer/agrichemicals were each targeted with 8,500 cpm* of the corresponding radioactive $^{14}C$ doctored agrichemical and then introduced at a rate of 5 lbs/acre into the top of an open bottom plexiglass 7 cm diameter, 8 cm long column containing 450 g of Polk County Florida surface soil. Then, water at room temperature was added in 4 increments of 125 ml. each to simulate 4 pore volumes i.e. normal rain conditions. The $^{14}C$ activity in each of the effluent solutions was assayed and the relative % of agrichemical recovered compared to 100% recovery in the absence of the present polymer is reported in the following Table VI. *curie/million

TABLE VI

| | | % Agrichem in Effluent | | | | |
| --- | --- | --- | --- | --- | --- | --- |
| Example | Sample of Ex. | First Pore V. | Second Pore V. | Third Pore V. | Fourth Pore V. | Total |
| XC | LXX | 6.9 | 17.0 | 19.1 | 16.3 | 59.3 |
| XCI | LXXIV | 11.4 | 59.1 | 12.9 | 2.6 | 86.0 |
| XCII | LXXVIII | 13.1 | 31.8 | 14.4 | 35.0 | 94.3 |
| XCIII | LXXXVI | 7.7 | 41.2 | 19.6 | 5.8 | 74.3 |

The above data shows that by the fourth wash only a minimal amount of the agrichemical was leached out of the immediate vicinity (to a 8 cm depth) of the soil application site.

EXAMPLES XCIV-CXI

Blends of the polymers 7 and 8 and following polymers 9-12 were mixed with agrichemicals in commercial formulations containing surfactant, emulsifier and diluent were prepared as follows.

POLYMERS

9. GAFQUAT ® 755 precursor (Copolymer of 80% N-vinyl pyrrolidone/20% dimethylaminoethyl methacrylate) as a 50% aqueous solution.
10. GAFQUAT ® 755 which is 50% quaternized with dimethylsulfate.
11. GAFQUAT ® 755 which is 50% quaternized with sulfuric acid.
12. Dimethylaminoethyl methacrylate homopolymer.

Polymers 7-12 were each tested with commercial agrichemical liquid formulations D-F by adding 5 g. on 100% basis of the polymer to the formulation to provide a weight ratio of 1:1 polymer to agrichemical and diluted with water to form a solution containing 10 wt. % polymer and 10 wt. % agrichemical.

D. Banvel herbicide containing 40% Dicamba in 4 lbs/gal of water
E. Aatrex 4L containing 40.8% Atrazine
F. Dual containing 86.4% Metolachlor The resulting solutions were then targeted with 8,500 cpm of radioactive $^{14}C$ agrichemical of the same species. The resulting mixtures were individually added to the top of a separate column similar to that above at a rate of 5 lbs. agrichemical/acre and the leachates from each of the 4 water washings were collected and analyzed.

The column employed in this study was used at bulk density of soil at packing. Each pore volume of water applied on the top of the soil column was equivalent to 3.2 cm (1.28 inch) of rainfall. The amount of herbicide leached was calculated on the basis of $^{14}C$-herbicide applied and recovered from the leachate. The difference between these two values represented that which was adsorbed by the soil.

Controls were run under exactly the same conditions with the same agrichemicals, except that the inhibiting polymer of this invention was omitted. In each control 100% leaching of agrichemical occurred. The analysis of the leachate from each of the 4 pore volumes is reported in following Table VII.

Table VIII. The procedure for these examples is as follows.

The indicated polymer/agrichemical formulation was introduced into a 130 cm × 10 cm soil packed column. In these experiments, 2.5 cm simulated rainfall was used for Dicamba 7.5 cm simulated rainfall for Atrazine and Metolachlor was employed by adding water at the rate of 1.5 cm/hr. After leaching, the columns were allowed to drain overnight and split longitudinally into two halves. Each half was planted with alfalfa or rye grass (as indicated) in 5 cm spaced rows. The % injury as a function of herbicide movement at different heights are shown in Table VIII.

At every 15 cm from bottom of the column, a ridge of silicone was applied on the inside wall of each half of the column to prevent "edge flow" of water along the soil-wall interface. A PVC end-cap with a small drain hole was fitted to the bottom of the column and the columns were packed with Florida soil from respective depths to provide a Florida soil profile. Soil-packed columns were kept in upright position and the soil was saturated with water and allowed to drain overnight; after which the commercial formulation of herbicide (5 kg ai/ha) with or without polymers (5 kg/ha) was introduced to the top of the column. A 2 ml solution of each

TABLE VII

| | | Relative % of Agrichemical Recovered Compared To 100% Leaching with Control* | | | | | |
|---|---|---|---|---|---|---|---|
| Example | Polymer | Agrichemical | 1st Pore | 2nd Pore | 3rd Pore | 4th Pore | Total |
| XCIV | 7 | D | 1.5 | 39.9 | 12.8 | 5.2 | 59.4 |
| XCV | 8 | D | 40.3 | 18.1 | 2.5 | 3.5 | 64.4 |
| XCVI | 9 | D | 32.8 | 47.0 | 5.1 | 4.3 | 89.2 |
| XCVII | 10 | D | 59.5 | 29.3 | 2.8 | 1.7 | 93.3 |
| XCVIII | 11 | D | 50.8 | 35.5 | 0.1 | 6.3 | 92.6 |
| XCIX | 12 | D | 34.8 | 38.5 | 9.9 | 9.4 | 92.6 |
| C | 7 | E | 1.0 | 25.67 | 24.2 | 14.1 | 64.9 |
| CI | 8 | E | 15.6 | 20.6 | 12.2 | 35.3 | 83.7 |
| CII | 9 | E | 12.5 | 34.6 | 26.5 | 16.5 | 90.1 |
| CIII | 10 | E | 24.7 | 41.2 | 11.7 | 6.5 | 84.1 |
| CIV | 11 | E | 8.6 | 54.7 | 17.3 | 5.1 | 85.7 |
| CV | 12 | E | 22.5 | 35.2 | 21.3 | 19.4 | 98.4 |
| CVI | 7 | F | 21.5 | 18.0 | 13.8 | 9.3 | 62.6 |
| CVII | 8 | F | 12.7 | 30.5 | 18.4 | 11.2 | 72.8 |
| CVIII | 9 | F | 16.0 | 41.4 | 13.4 | 17.2 | 88.0 |
| CIX | 10 | F | 18.3 | 38.4 | 11.6 | 1.1 | 69.4 |
| CX | 11 | F | 15.3 | 40.3 | 6.7 | 11.6 | 73.9 |
| CXI | 12 | F | 14.2 | 44.0 | 14.9 | 13.3 | 86.4 |

*By $^{14}C$ activity assay using Scintillation counter, % Agrichemical

EXAMPLES CXII-CXXIX

Bioassays of selected samples (i.e. products of Examples XCIV-CXI) were made and results reported in treatment was applied uniformly on the soil surface as several drops using pasteur pipet. Columns were leached by pouring distilled water over filter paper placed on the soil surface to ensure uniform distribution of water and leaching was measured at 15, 30, 45, 60 and 60+cm depths.

TABLE VIII

| | % Alfalfa Injury (Application rate 5 kg/ha or 4.5 lbs/acre) | | | | | | |
|---|---|---|---|---|---|---|---|
| | Sample % | Column Depth (cm) | | | | | Total % |
| Example | of Ex. | 0-15 | 15-30 | 30-45 | 45-60 | 60-120 | Decrease |
| CXII | XCIV | 100 | 100 | 92 | 42 | 0 | 16 |
| CXIII | XCV | 100 | 100 | 100 | 50, 67 | 0 | 8, 12 |
| CXIV | XCVI | 100 | 100 | 100 | 42 | 0 | 14 |
| CXV | XCVII | 100 | 100 | 100 | 83 | 0 | 4 |
| CXVI | XCVIII | 100 | 100 | 100 | 100 | 0 | 0 |
| CXVII | XCIX | 100 | 100 | 100 | 100 | *0 | 0 |
| CXVIII | C | 100 | 83 | 0 | 0 | 0 | 8 |
| CXIX | CI | 100 | 50 | 0 | 0 | 0 | 25 |
| CXX | CII | 100 | 83 | 0 | 0 | 0 | 8 |
| CXXI | CIII | 100 | 58 | 0 | 0 | 0 | 21 |
| CXXII | CIV | 100 | 41 | 0 | 0 | 0 | 29 |
| CXXIII | CV | 100 | 33 | 0 | 0 | 0 | 33 |

TABLE VIII-continued

% Rye Grass Injury (Application rate 10 kg/ha or 8.9 lbs/acre)

| Example | Sample % of Ex. | Column Depth (cm) 0-15 | 15-30 | 30-120 | Total % Decrease |
|---|---|---|---|---|---|
| CXXIV | CVI | 100 | 66 | 0 | 17 |
| CXXV | CVII | 100 | 67 | 0 | 17 |
| CXXVI | CVIII | 100 | 100 | 0 | 0 |
| CXXVII | CIX | 100 | 83 | 0 | 8 |
| CXXVIII | CX | 100 | 83 | 0 | 8 |
| CXXIX | CXI | 100 | 100 | 0 | 0 |

Controls with no polymer gave 100% injury at all levels from 0-30 cm for metolachlor.
Controls with no polymer gave 100% injury at all depths from 0-60 cm for Dicamba (D) and 0-30 cm for Atrazine (E).

The above examples illustrate various embodiments and preferred leach inhibiting compositions of this invention; however, it will be understood that substitutions of the crop treating chemicals referred to in the foregoing description, or their mixtures, can be made to replace those used in the respective Examples without departing from the scope of this invention. Similarly, any of the lactam polymers set forth in the disclosure, or their mixtures, can be substituted for those employed in the above Examples, to provide leach inhibition of the agrichemical selected. From the above description, it will also become apparent that many modifications and alterations can be made in the preparations of the leach inhibiting compositions which are within the scope of this invention.

What is claimed is:

1. An agrichemical leach inhibiting composition comprising an active plant growth regulating agrichemical and a leach inhibiting amount of a crosslinked or non-crosslinked N-alkenyl lactam homopolymer or a copolymer with a $C_2$ to $C_{30}$ comonomer selected from the group of an alkenoic acid; alkenyl anhydride, alkenyl ester, alkenyl ether, optionally quaternized alkenyl amino amide, optionally quaternized alkenyl amino ester, an alpha mono- or di- olefinically unsaturated comonomer, and terpolymeric mixtures of said comonomers.

2. The composition of claim 1 wherein the weight ratio of agrichemical to polymer is between about 0.1:1 and about 10:1.

3. The composition of claim 2 wherein the weight ratio of agrichemical to polymer is between about 0.3:1 and about 2:1.

4. The composition of claim 1 wherein said lactam moiety is represented by the formula

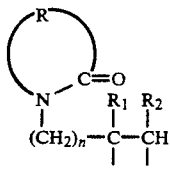

wherein R is $C_3$ to $C_6$ alkylene optionally substituted with $C_1$ to $C_{20}$ alkyl; $R_1$ and $R_2$ are each independently hydrogen or $C_2$ to $C_{20}$ alkyl and n has a value of from 0 to 1 or a mixture of said lactam radicals.

5. The composition of claim 4 wherein R is $C_3$ alkylene and one of $R_1$ and $R_2$ is hydrogen.

6. The composition of claim 5 wherein said polymer is a crosslinked homopolymer.

7. The composition of claim 5 wherein said polymer is a crosslinked copolymer.

8. The composition of claim 5 wherein said polymer is a linear copolymer.

9. The composition of claim 8 wherein said comonomer is vinyl acetate.

10. The composition of claim 8 wherein said comonomer is acrylic acid.

11. The composition of claim 6 wherein said lactam homopolymer is linear homopolymer alkylated with an alpha olefin.

12. The composition of claim 11 wherein said olefin is $C_{20}$ alpha olefin.

13. The composition of claim 4 wherein said comonomer is a quaternized or non-quaternized dimethylaminoethyl methacrylate.

14. The composition of claim 1 wherein said leach inhibiting agent is the polymer of N-vinyl pyrrolidone, N-vinyl caprolactam and dimethylaminoethyl methacrylate.

15. The composition of claim 1 wherein the polymer contains from 0 to 90 wt. % of said comonomer.

16. The composition of claim 15 wherein the number average molecular weight of said polymer is between about 5,000 and about 200,000.

17. The composition of claim 15 wherein the polymer contains 0 to 85 wt. % of said comonomer.

18. The composition of claim 17 wherein the number average molecular weight of said polymer is between about 6,000 and about 150,000.

19. The composition of claim 2 wherein said polymer and said agrichemical are complexed.

20. The composition of claim 2 wherein said polymer and said agrichemical are blended to form a mixture.

21. The composition of claim 2 wherein said agrichemical is encapsulated in said lactam containing polymer.

22. The composition of claim 21 wherein said lactam-containing polymer is a non-crosslinked polymer of N-vinyl pyrrolidone, N-vinyl caprolactam and dimethylaminoethyl methacrylate.

23. The composition of claim 21 wherein said lactam-containing homopolymer is a crosslinked homopolymer of N-vinyl pyrrolidone.

24. A method of inhibiting leaching of an active plant growth regulating agrichemical which comprises contacting a plant or plant site with a leach inhibiting amount of the composition of claim 1.

25. The method of claim 24 wherein said composition is applied in a dry particulate state.

26. The method of claim 24 wherein said composition is applied as an aqueous solution or emulsion containing an effective leach inhibiting amount of said polymer.

* * * * *